United States Patent [19]
Pohle et al.

[11] Patent Number: 5,906,273
[45] Date of Patent: May 25, 1999

[54] ARMED SUTURE PACKAGE WITH UNIVERSAL DISPENSING CAPABILITY

[75] Inventors: Michael S. Pohle, Flemington; Marvin Alpern, Glen Ridge, both of N.J.; Robert J. Cerwin, Pipersville, Pa.

[73] Assignee: Ethicon, Inc., Somerville, N.J.

[21] Appl. No.: 08/986,215

[22] Filed: Dec. 5, 1997

[51] Int. Cl.⁶ ................................................. A61B 17/06
[52] U.S. Cl. ............................................................ 206/63.3
[58] Field of Search ................................. 206/63.3, 227, 206/380, 382, 495

[56] References Cited

U.S. PATENT DOCUMENTS

| 4,699,271 | 10/1987 | Lincoln et al. ........................ 206/63.3 |
| 4,961,498 | 10/1990 | Kalinski et al. . |
| 4,967,902 | 11/1990 | Sobel et al. . |
| 5,052,551 | 10/1991 | Cerwin et al. . |
| 5,056,658 | 10/1991 | Sobel et al. . |
| 5,180,053 | 1/1993 | Cascio et al. . |
| 5,213,210 | 5/1993 | Cascio et al. . |
| 5,230,424 | 7/1993 | Alpern et al. . |
| 5,236,083 | 8/1993 | Sobel et al. . |
| 5,249,673 | 10/1993 | Sinn ....................................... 206/63.3 |
| 5,284,240 | 2/1994 | Alpern et al. . |
| 5,655,652 | 8/1997 | Sobel et al. . |

Primary Examiner—David T. Fidei

[57] ABSTRACT

A suture package having a shallow polymer tray for holding an armed suture has a substantially flat floor area, an exterior surface of which defines at least a portion of a rear surface of the package. A front cover forms a front surface of the package and a needle park is disposed on the floor area for holding a surgical needle of the armed suture. The floor area has a window therethrough proximate the needle park. The front cover terminates proximate the needle park to provide an access opening to the needle. The window and the access opening permit the needle to be grasped by a needle holder and to be withdrawn from the package. Because the package has an opening on both the front and rear surfaces for viewing and removing the needle, curved needles may be stored therein in a conventional orientation, i.e., to serve right-handed physicians while at the same time accommodating dispensing from the rear to provide a suitable needle orientation for use by left-handed surgeons.

17 Claims, 4 Drawing Sheets

ARMED SUTURE PACKAGE WITH UNIVERSAL DISPENSING CAPABILITY

FIELD OF THE INVENTION

The present invention relates to packages for storing and dispensing surgical needles and attached suture filaments, and more particularly to a package facilitating the dispensing of armed sutures such that one type of suture package is suitable to dispense an armed suture in the proper orientation for use by either a right-handed or a left-handed surgeon.

BACKGROUND OF THE INVENTION

Numerous types of packages and packaging methods have been proposed over the years for economically and reliably delivering or relaying an "armed" suture i.e., a suture having a surgical needle attached, to a surgeon in a sterile condition. Besides maintaining sterility of the armed suture, its packaging must also provide convenient dispensing of the suture under the demanding conditions of surgery. Examples of modern suture packaging are disclosed in U.S. Pat. No. 4,967,902 to Sobel et al. and U.S. Pat. No. 5,052,551 to Cerwin et al. Both of these patents are owned by the assignee herein and disclose a generally oval suture package having a central needle park for holding or "parking" the surgical needle and a peripheral channel for receiving the suture filament attached to the needle. Due to the clearance between successive filament loops and the suture channel, the shape of the channel, and the material composition of the package, the suture can be withdrawn from the package without binding in the suture channel.

One of the functions of armed suture packaging is to hold or position the needle such that it can be readily and securely grasped with a suitable needle holder. In grasping the needle with the needle holder, it is desired that the package present the appropriate portion of the needle for grasping, i.e., towards the upper ¼ of the needle proximate the suture end of the needle, and that the needle when grasped is in the correct orientation for use by the surgeon. This is particularly true with respect to curved needles which have an inherent directional sense and which therefore must be properly oriented in order to execute standard surgical technique, as discussed more fully below. Since the package may be used to present the needle at a specific orientation, a convention has been established as to needle orientation to promote efficiency and predictability in the operating room.

While suture manufacturers could produce specific packaging for left-handed and right-handed persons, it would complicate the surgical team's already complicated and demanding job, requiring that supplies for left and right handed surgeons by maintained and representing yet another detail to be monitored to prepare for and conduct surgery, i.e., to make sure that all the various sutures to be made available for use are of the correct handedness for the particular surgeon(s). As a result, presently available armed suture packages are oriented for use by right-handed persons. This is simply due to the facts that one or the other of the two orientations must be selected and that there are more right-handed persons than left-handed persons. Consequently, needles dispensed for left-handed surgeons must be manually reorientated in the needle holder by the scrub nurse or the surgeon prior to use. It would therefore be desirable to have a package for an armed suture that preserves the present simple needle orientation conventions while at the same time offering an accommodation to left-handed surgeons.

SUMMARY OF THE INVENTION

The problems and disadvantages associated with known suture packaging and methods for using same are overcome by the present invention which includes a suture package having a shallow polymer tray for holding an armed suture and with a substantially flat floor area, an exterior surface of which defines, at least partially, a rear surface of the package. A front cover forms a front surface of the package and a needle park is disposed on the floor area for holding a surgical needle of the armed suture. The floor area has a window therethrough proximate the needle park. The front cover terminates proximate the needle park to provide an access opening to the needle. The window and the access opening permit the needle to be grasped by a needle holder and to be withdrawn from the package.

BRIEF DESCRIPTION OF THE FIGURES

For a better understanding of the present invention, reference is made to the following detailed description of an exemplary embodiment considered in conjunction with the accompanying drawings, in which.

DETAILED DESCRIPTION OF THE FIGURES

Figure 1:
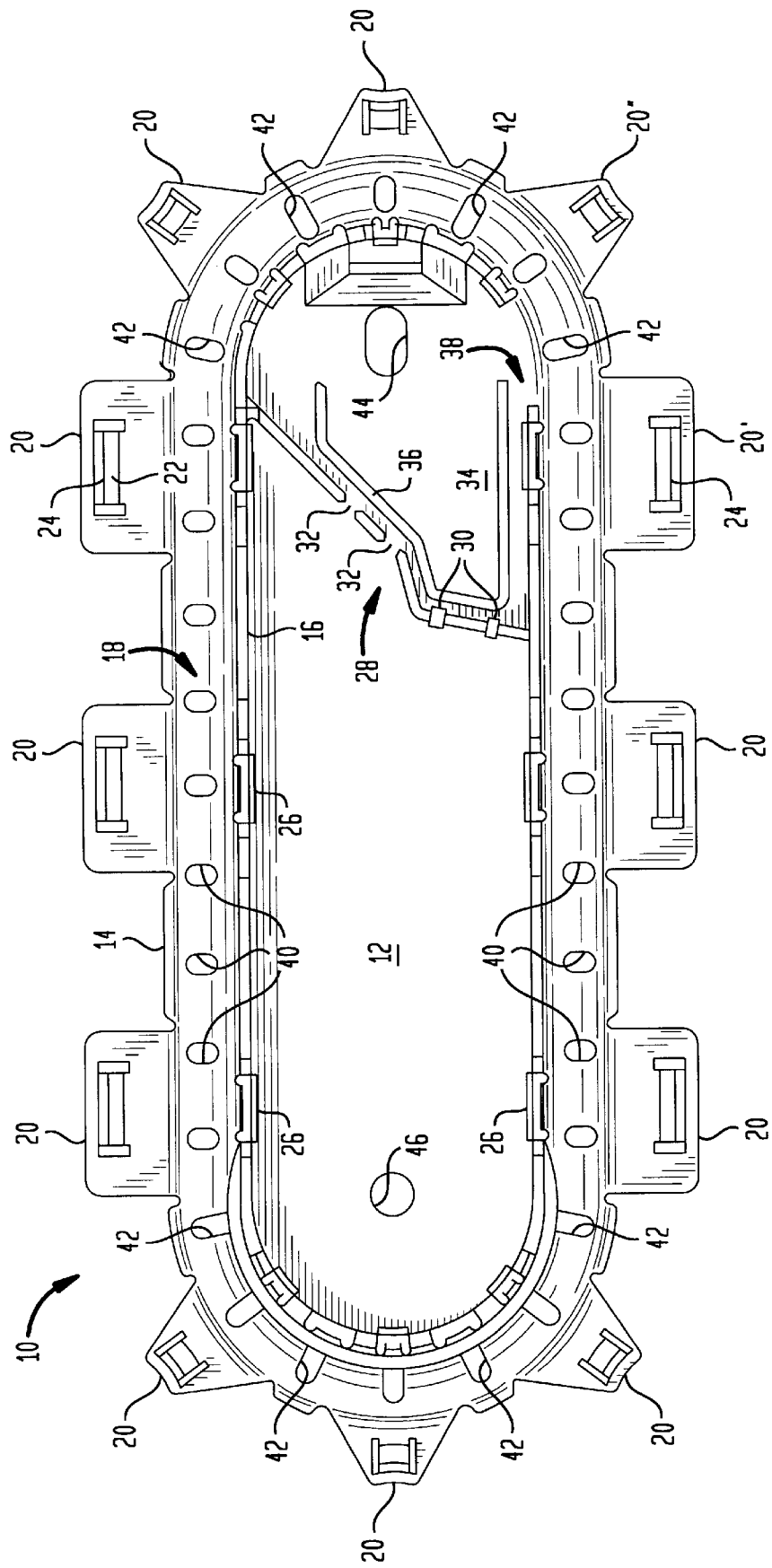
FIG. 1 is a plan view of a prior art suture package.

FIG. 1 shows an empty, unfolded, suture package 10 in accordance with the prior art. The package 10 is primarily a shallow oval pan or tray with a central floor area 12 and a raised edge 14 that curves up from the plane of the floor area 12 to a predetermined height thereabove and to a terminal orientation of about 90 degrees relative to the floor area 12. An inner peripheral wall 16 extends at substantially right angles to the floor area 12 substantially coextensively with the raised edge 14, defining a trough or channel 18 with a generally U-shaped cross-section for receiving a coil of suture filament (not shown). Suture retaining tabs 20 are hingedly connected, e.g., by "living" plastic hinges, to the raised edge 14 and have latch openings 22 and latch projections 24 to engage mating latch posts 26 projecting from the inner peripheral wall 16. After the suture is laid in the channel 18, the tabs 20 can be bent inwardly and over the channel 18 for retaining the coil of suture filament. The latch projections 24 and latch posts 26 cooperate to retain the tabs 20 in the closed position.

A needle park 28 for holding the surgical needle extends from the floor area 12 proximate one end of the package 10. The needle park includes pairs of undercut and rigid needle holders 30 and 32. The package floor beneath needle holders 30 has been undercut to enable tapered ends of the overlying needle holders 30 to flex and bend somewhat when a needle is inserted therein. Thus, the undercut needle holders 30 can accommodate a wider range of needle gauges than the rigid needle holders 32 can accommodate. Adjacent the needle park 28 is a relief flap 34 defined by a cutout 36. A portion of the inner wall 16 is eliminated in the vicinity of the needle park 28 to form a vent 38 in the channel 18 through which the suture extending from the needle accesses the channel 18 between tabs 20' and 20".

The bottom of the channel 18 is periodically perforated by holes 40 and 42 around the circumference thereof to assist in packaging an armed suture as follows: Package 10 is placed on an assembly platform that has a number of upwardly extending pins. Two of the pins are aligned to extend upward through holes 44 and 46 in the center of the package to retain the package in its assembly position on the platform. Eight other pins extend upward and are aligned to pass through the holes 42 of the channel 18. The platform is open beneath the remaining channel holes 40 and a vacuum source below the platform draws air through the holes 40. With the package so emplaced, the needle is located in one of the needle parks 30, 32 of the needle holder 28, and the suture is looped above the pin extending through the hole 44 then downward through the vent 38 and into the suture channel 18. The suture is then wound in a clockwise direction around the pins which extend through the channel holes 42.

Additional details regarding the construction and use of the suture package of FIG. 1 appear in U.S. Pat. Nos. 4,967,902 and 5,052,551. Both of these patents are incorporated herein by reference.

The sutures which may be packaged in the packages shown in FIG. 1 include any of the conventional sutures, absorbable and non-absorbable, such as silk, polypropylene, polydioxanone, and the like and equivalents thereof. The sutures may be braided, woven or monofilament and the needles may be tapered or cutting point, curved, semi-curved, or straight. The sutures are typically mounted to the ends of surgical needles by conventional processes such as swaging.

A variety of materials can be used to form the suture package described in relation to FIG. 1 above, including polyester, polyethylene, polyvinyl chloride, polystyrene and polypropylene. In general, it is desirable to utilize different materials for the packaging than for the sutures to prevent "gauling" or "lock-ups" when the suture is removed from the package.

As can be appreciated from FIG. 1, the suture package 10 is asymmetrical in the direction of extension of the inner peripheral wall, i.e., in the viewing direction of the plan view, due to the fact that all the features of the package extend unidirectionally from the floor area 12 of the package. More specifically, the inner wall 16, the needle park 28, the peripheral edge 14, etc. all extend in the same direction away from the floor area 12. As a result of the foregoing asymmetry, packages manufactured in accordance with this design have an inherent directionality that leads to a specific orientation of the package when grasped by a surgeon or scrub nurse. More specifically, a right-handed person would likely grasp the package in the left-hand with the needle park facing them and pointed toward the thumb side of the hand. In this manner, the package can be securely grasped by the left hand with the needle exposed for removal by a needle holder controlled by the more dexterous right hand. When used by a left-handed person, the package would be held in the right-hand with the needle park facing them and pointed toward the thumb side of the hand. The needle would then be grasped and dispensed by a needle holder (needle nosed plier/hemostat) held in the more dexterous left hand. The implications of this inherent package orientation during use can be further appreciated by examining FIG. 2.

Figure 2:
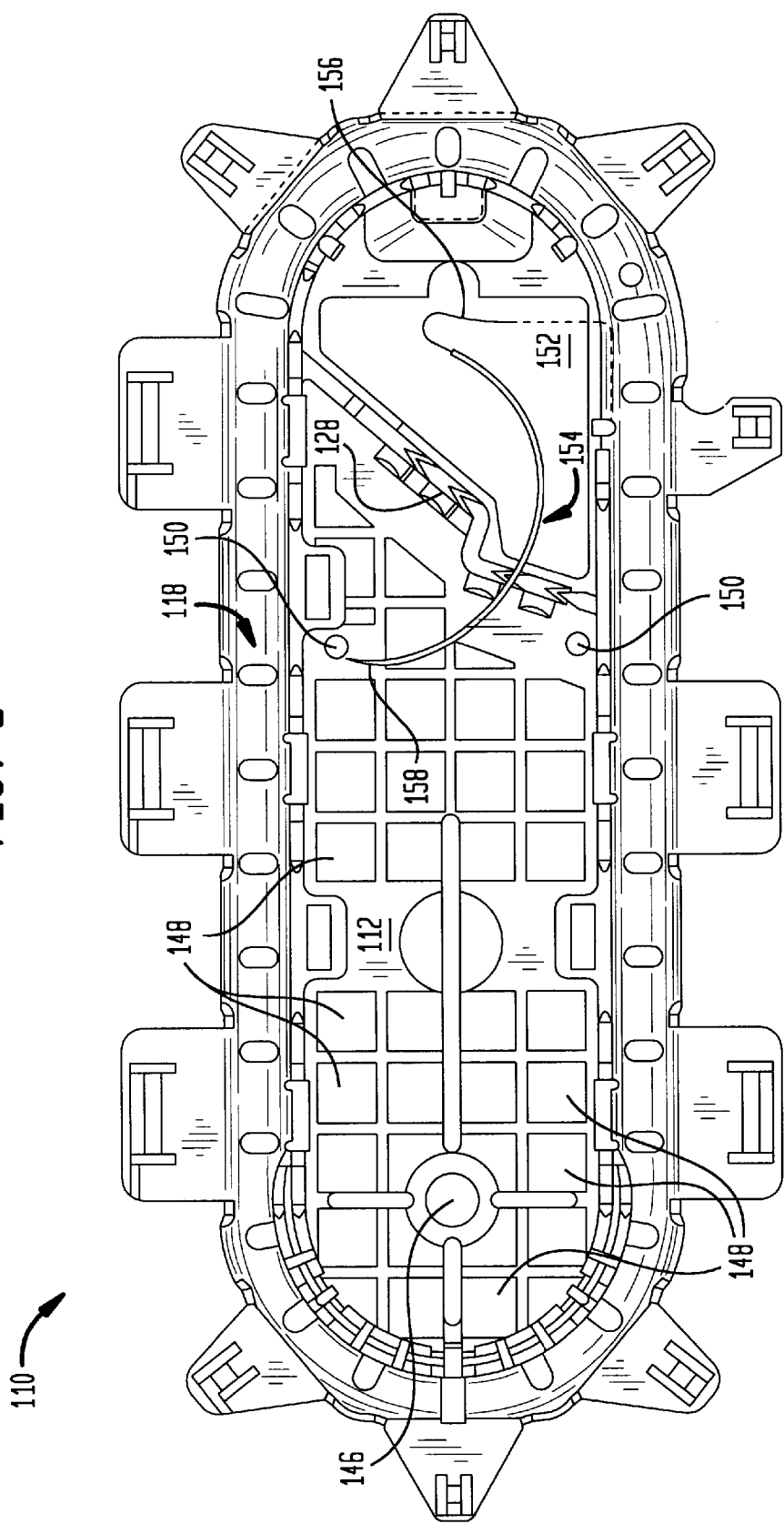
FIG.2 is a front plan view of a suture package in accordance with the present invention.

FIG. 2 shows a suture package 110 in accordance with the present invention. One can readily appreciate from comparing FIG. 2 to FIG. 1 that there are substantial similarities between the prior art device and the present invention. To more clearly illustrate the relationship between FIGS. 1 and 2, a numbering convention is adopted herein in which elements of the invention depicted in FIG. 2 which are similar to those depicted in FIG. 1 are given the same reference number increased by 100.

With the foregoing prefatory comments in mind, the primary difference between the present invention and the prior art depicted in FIG. 1 is the presence of a plurality of fenestrations 148 in the central floor area 112 and the presence of a window 152 in the central floor area above the needle park 128. The significance of the fenestrations 148 is explained fully in a co-pending application by the inventors herein and entitled FENESTRATED SUTURE PACKAGE, U.S. Serial Number (not assigned yet) which was filed contemporaneously herewith and is incorporated by reference herein. One can note briefly however that the fenestrations are beneficial in that they promote dimensional conformity of the package to the design configuration due to the relief of internal material stresses. The fenestrations also provide savings on material usage and solid waste disposal. Window 152 likewise promotes the foregoing benefits achieved by the fenestrations 148. Furthermore, window 152 allows the package 110 to be utilized efficiently by left and right handed persons while preserving existing packaging conventions. More particularly, FIG. 2 illustrates the position of a needle 154 in needle park 128 in accordance with convention and for use by right-handed persons. Needle 154 has a suture 156 (partially shown in phantom view) extending from an end thereof and entering the suture channel 118 proximate one end of the package 110. The needle 154 arcs downwardly in a clockwise direction to its point 158.

Figure 3:
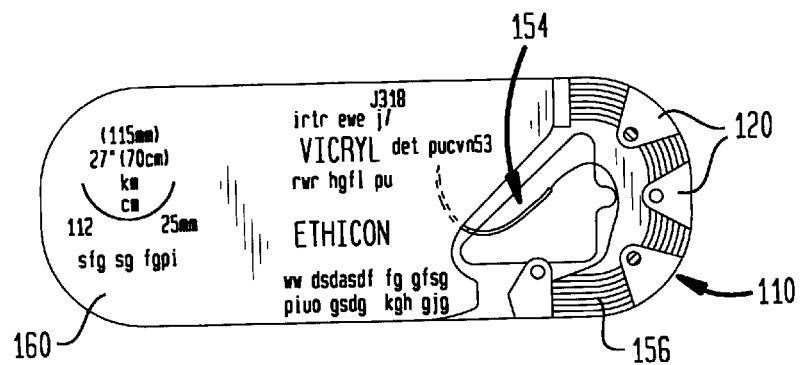
FIG. 3 is a front plan view of the suture package of FIG. 2 with suture and labelling incorporated therewith.

FIG. 3 shows a suture package 110 that has been filled with suture 156 retained by tabs 120. One of the functions of armed suture packaging is to safely store the needle to prevent inadvertent injury by the needle's sharp point 158. This is accomplished by shielding the lower end of the needle 154 with a cover 160 as shown in FIG. 3. The cover also serves to prevent contamination of the needle through unnecessary contact with the surgeon's or scrub nurse's gloved hand and provides a surface for product labelling.

Figure 4:
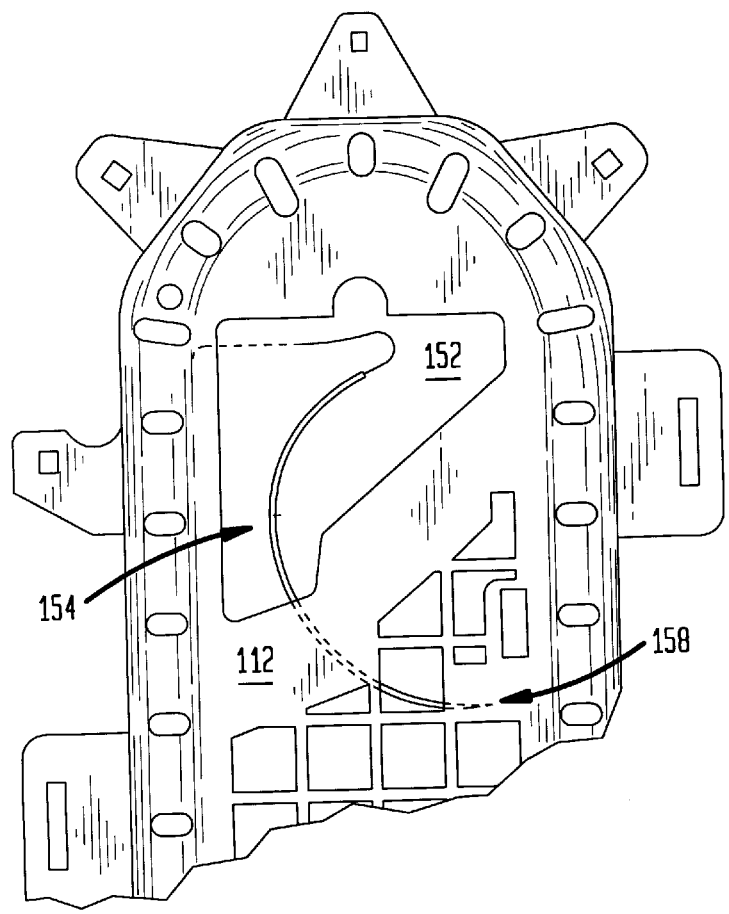
FIG. 4 is a fragmentary view of the rear surface of the suture package of FIG. 2.

FIG. 4 shows the package 110 of FIG. 2 from the rear. As can be appreciated from FIG. 4, the point 158 of the needle 154 is shielded by the floor area 112, preventing inadvertent needle sticks and contamination of the needle. The needle 154, when viewed through window 152, has a reversed orientation relative to FIGS. 2 and 3. Namely, the needle arcs downwardly in a counter-clockwise direction. Whereas FIGS. 2 and 3 depict a conventional needle orientation suitable for use by right-handed persons, FIG. 4 displays an orientation suitable for use by left-handed persons. The underlying reasons for the significance of needle orientation shall now be described.

The preferred technique for suturing a wound involves correct needle orientation. More specifically, the wound to be closed is preferably positioned generally near the centerline of the surgeon's field of view and between the surgeon's left and right hands. In using an arcuate needle, the right-handed surgeon utilizes a needle holder grasped in the right hand. The needle is positioned with the suture end of the needle extending upward and the needle point downward. The needle curves clockwise from top to bottom from the perspective of the surgeon. To suture, the surgeon rotates his/her hand counterclockwise towards its limit of travel (the human hand forearm is limited to about 180° of rotation) and then inserts the point of the needle into the tissue to be sutured. The needle is then rotated clockwise through the tissue to be sutured and towards the centerline of the surgeon's field of view. In the case of a left-handed surgeon, the needle holder is held in the left hand with the needle curving downward to the point in a counterclockwise direction. Suturing is done in the counterclockwise direction and towards the centerline of the surgeon's field of view.

Figure 5:
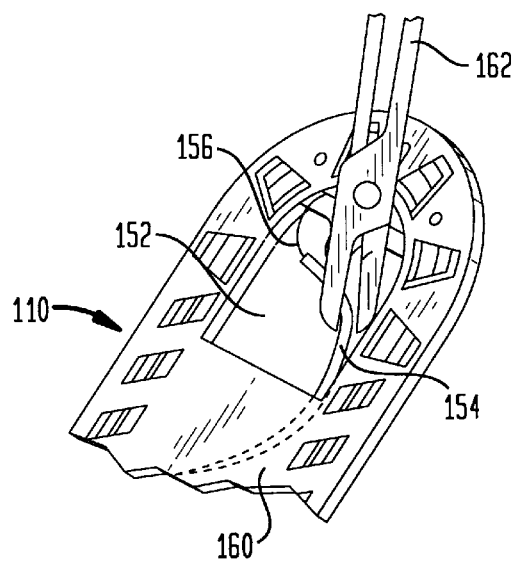
FIGS. 5 and 6 are diagrammatic depictions of a needle holder dispensing the armed suture for right-handed and left-handed use, respectively.
Figure 6:
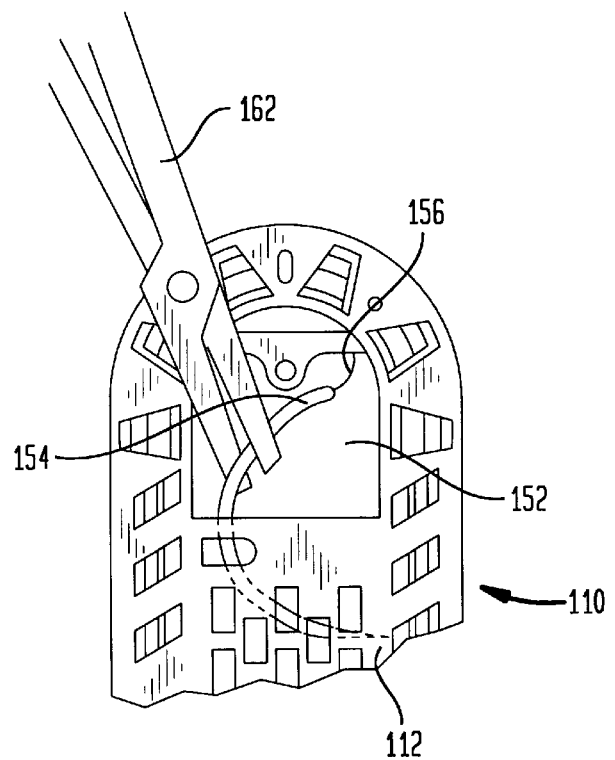

FIGS. 5 and 6 illustrate diagrammatically how the present invention can be utilized to provide the correct orientation of the needle such that the package 110 dispenses armed sutures for use by both right-handed and left-handed surgeons. In FIG. 5, the needle holder is inserted into the front of the package 110 above the front cover 160 to grip the needle 154 in an orientation that would be suitable for use by a right-handed surgeon. The needle 154 can be withdrawn from the package 110 and will be positioned on the needle holder 162 with the suture 156 uppermost and the needle 154 arcing down in a clockwise direction to its point.

In FIG. 6, the package 110 has been rotated such that the underside of the floor area 112 faces the viewer. The needle holder 162 is inserted through the window 152 to grip the needle 154 in an orientation suitable for use by a left-handed surgeon. The needle 154 can be withdrawn from the package 110 and will be positioned in the needle holder 162 with the suture 156 uppermost and the needle 154 arcing down in a counterclockwise direction to its point.

Note that the overall design of the package, i.e., with the window 152 left open and without any backing, preserves the required function of visualizing the upper portion of the needle 154 by positioning it against a contrasting background. For example, it would not be desirable for the package 110 to have an aluminum overwrapping that would be visible through the window when dispensing for right-handed surgeons. If this were attempted, the aluminum would not provide sufficient contrast with the metal needle to readily locate and grasp the needle.

It is preferred that the window 152 be formed in the package 110 as part of the original molding process rather than being perforated or die cut into a non-windowed blank. This method of formation of the window 152 is consistent with one of the benefits of the present invention, namely, that the window 152 results in a decrease in material usage for forming the package 110 and a corresponding decrease in the amount of waste product represented by the package itself. For example, the package 110 of FIG. 1 uses at least 5% less polymer than an otherwise identical, non-windowed package. The economy of material usage associated with the present invention results in a lighter product which costs less to ship and handle relative to its non-windowed counterpart.

The paper cover 160 of the suture package 110 may be imprinted with an identification of the suture material contained in the package, as well as other identification information such as lot number and manufacturer identification, and is completed for shipping by overwrapping with foil and optionally with a polymer film. Overwrapping of this type is well known in the field, as are the proper procedures for maintaining sterility of the suture during the assembly of the sealed suture package. Accordingly, such conventional processes shall not be described herein. When the suture package is used, the plastic overwrapping, if provided, can be removed in the non-sterile field. The foil wrapping can then be removed in the course of transfer from the non-sterile field to the sterile field, for example, the circulating nurse can strip back the foil wrapping and the scrub nurse can withdraw the suture package from the foil overwrapping and place it on a mayo stand. As a consequence, neither the surgeon nor the scrub nurse is required to tear open the suture package in the sterile field. The suture package can therefore be described as offering a one-step presentation. Because the package is overwrapped in foil, sterility is preserved notwithstanding the window 152 in the central floor area 112.

It should be understood that the embodiments described herein are merely exemplary and that a person skilled in the art may make many variations and modifications without departing from the spirit and scope of the invention as defined in the appended claims. For example, whereas the present disclosure describes the invention herein as including a window having a generally triangular shape. Any window shape could be employed. Also, whereas a generally oval-shaped suture package is shown in the application, other package shapes, such as circular or polygonal could be employed. All such variations and modifications are intended to be included within the scope of the invention as defined in the appended claims.

We claim:

1. A suture package, comprising a shallow polymer tray for holding an armed suture and having a substantially flat floor area with an upturned peripheral edge, an exterior surface of said floor area defining at least a portion of a rear surface of said package; a front cover disposed on said peripheral edge forming a front surface of said package, said front cover spaced from said floor area; a needle park disposed on said floor area for holding a surgical needle of said armed suture with a point of said surgical needle being disposed between said front cover and said floor area in a position shielding said point of said needle from inadvertent contact when said package is handled, said floor area having a window therethrough proximate said needle park, said front cover terminating proximate said needle park to provide an access opening to a portion of said needle intermediate said point and an opposite end thereof, said window and said access opening permitting said needle to be grasped by a needle holder and permitting said needle to be withdrawn from said package.

2. The package of claim 1, further including an armed suture with a needle, said needle being curved and when installed in said package curves in a plane which is generally parallel to said floor area, said curvature going clockwise from suture to needle point when viewed from one of said front surface and said rear surface and counter-clockwise when viewed from the other of said front surface and rear surface.

3. The package of claim 2, wherein said clockwise orientation is that required by right-handed surgeons and said counter-clockwise orientation is that required by left-handed surgeons and said package can selectively dispense said needle in said clockwise and counter-clockwise orientations.

4. The package of claim 3, wherein said orientation of said needle positioned in said needle park is clockwise when viewed from said front surface and counterclockwise when viewed from said rear surface, said needle being dispensed in the clockwise orientation through said access opening and in the counter-clockwise orientation through said window.

5. The package of claim 4, wherein said access opening is approximately aligned with said window such that light may pass through said package via said access opening and said window.

6. The package of claim 5, wherein said access opening and said window have approximately the same open area.

7. The package of claim 6, wherein said needle park is located proximate to an edge of said access opening and proximate to an edge of said window.

8. The package of claim 7, wherein said window is approximately triangular in shape.

9. The package of claim 6, wherein said package has an elongated oval shape.

10. The package of claim 9, wherein said window is disposed proximate an end of said elongated oval package.

11. The package of claim 10, wherein said package has a plurality of fenestrations in said floor area.

12. The package of claim 3, wherein said needle when positioned within said package has a conventional orientation suitable for use by a right-handed individual.

13. The package of claim 3, wherein said needle is positioned within said package with an end receiving said suture being viewable through said access opening and said window and an end of said needle being shielded by said front cover and said floor area.

14. A suture package, comprising a shallow polymer tray for holding an armed suture and having a substantially flat floor area with an upturned peripheral edge, a cover on said peripheral edge spaced from said floor area and a needle park disposed on said floor area for holding a surgical needle, said floor area and said cover each having a window therethrough proximate said needle park, the window of said cover permitting a needle held by said needle park to be grasped and withdrawn by a needle holder inserted through said window of said cover from one side of said package and the window of said floor area permitting a needle held by said needle park to be grasped and withdrawn by a needle holder inserted through said window of said floor area from the other side of said package window permitting a needle held by said needle park to be grasped by a needle holder from either.

15. The package of claim 14, wherein said needle is curved and when installed in said package curves in a plane which is generally parallel to said floor area, said curvature going clockwise from suture to needle point when viewed from one of said front surface and said rear surface and counter-clockwise when viewed from the other of said front surface and rear surface, said clockwise orientation being that required by right-handed surgeons and said counter-clockwise orientation being that required by left-handed surgeons.

16. The suture package of claim 1, further including a suture trough extending around the periphery of said floor area and wherein said upturned peripheral edge is a terminal edge of said suture trough.

17. The suture package of claim 14, further including means for receiving a coil of suture extending from said needle, said means for receiving being disposed peripherally about said floor area and said window in said floor area.

\* \* \* \* \*

UNITED STATES PATENT AND TRADEMARK OFFICE
CERTIFICATE OF CORRECTION

PATENT NO : 5,906,273
DATED : May 25, 1999
INVENTOR(S): Michael S. Pohle, et al.

It is certified that error appears in the above-identified patent and that said Letters Patent are hereby corrected as shown below:

Claim 14, Column 8, line 1, after "said package", delete "window permitting a needle held by said needle park to be grasped by a needle holder from either"

Signed and Sealed this

Fourteenth Day of December, 1999

Attest:

Attesting Officer

Q. TODD DICKINSON

Acting Commissioner of Patents and Trademarks